United States Patent [19]

Kaiser

[11] Patent Number: 4,527,001

[45] Date of Patent: Jul. 2, 1985

[54] SMALL OLEFIN INTERCONVERSIONS

[75] Inventor: Steven W. Kaiser, South Charleston, W. Va.

[73] Assignee: Union Carbide Corporation, Danbury, Conn.

[21] Appl. No.: 551,888

[22] Filed: Nov. 15, 1983

[51] Int. Cl.$^3$ .......................... C07C 3/16; C07C 3/32; C07C 5/22

[52] U.S. Cl. .................................. 585/643; 585/513; 585/514; 585/528; 585/667; 585/671; 585/651; 585/653

[58] Field of Search ............... 585/513, 514, 528, 643, 585/667, 671, 651, 653

[56] References Cited

U.S. PATENT DOCUMENTS

| | | |
|---|---|---|
| 3,756,942 | 9/1973 | Cattanach .......................... 585/407 |
| 3,760,024 | 9/1973 | Cattanach .......................... 585/417 |
| 3,775,501 | 11/1973 | Kaeding et al. ..................... 585/414 |
| 3,827,968 | 8/1974 | Givens et al. ....................... 585/322 |
| 4,021,502 | 5/1977 | Plank et al. ......................... 585/533 |
| 4,150,062 | 4/1979 | Garwood et al. .................... 585/415 |
| 4,227,992 | 10/1980 | Garwood et al. .................... 585/650 |
| 4,254,295 | 3/1981 | Tabak .................................. 585/533 |
| 4,392,984 | 7/1983 | Engelbach et al. ................. 585/514 |

*Primary Examiner*—D. E. Gantz
*Assistant Examiner*—A. Pal
*Attorney, Agent, or Firm*—Gary L. Wamer

[57] ABSTRACT

The process for the interconversion of "small olefins" selected from the class consisting of ethylene, propylene, butenes and mixtures thereof comprising contacting said small olefin(s) with non-zeolitic molecular sieves.

17 Claims, No Drawings

SMALL OLEFIN INTERCONVERSIONS

FIELD OF THE INVENTION

The instant invention relates to the use of specific new non-zeolitic molecular sieves for the interconversion of $C_2$ to $C_4$ olefins whereby feedstocks containing a given molar amount of ethylene, propylene, butenes and derivatives thereof or mixtures thereof and are converted to an olefinic mixture having substantially different molar amounts of ethylene, propylene or butenes.

BACKGROUND OF THE INVENTION

Processes for various conversions of low molecular weight olefins are well known in the prior art. Representative of such general conversion processes are U.S. Pat. Nos.: 3,140,249; 3,140,251; 3,140,253; 3,140,322; and 2,972,643.

The conversion of paraffins, olefins and/or naphthenes to aromatics using a ZSM-5 catalyst is disclosed in U.S. Pat. No. 3,756,942. The conversion of olefins to aromatics by use of ZSM-5 and ZSM-8 is disclosed in U.S. Pat. No. 3,760,024. The prior art relating to olefin conversion over ZSM-type catalysts also includes numerous process related patents including: U.S. Pat. No. 3,775,501 (co-feed air with olefins over ZSM-5); U.S. Pat. No. 3,827,968 (ZSM-5 in a two step process); U.S. Pat. No. 3,960,978 (ion-exchange and/or steamed ZSM-5 or ZSM-11); U.S. Pat. No. 4,021,502 (olefin conversion using ZSM-5, ZSM-12, ZSM-18, chabazite and beta zeolite under controlled process conditions); U.S. Pat. No. 4,150,062 (use of co-fed water with olefins over ZSM-5); U.S. Pat. No. 4,227,992 (ethylene/propylene conversion over ZSM-12 employing controlled process conditions).

The above processes employ the aluminosilicates generally known as "ZSM-type" aluminosilicates. (The term "ZSM-type" is generally employed in the literature to denominate the aluminosilicates assigned a "ZSM-n" name where "n" is an integer.) Accordingly, such processes do not relate to a process or processes not employing aluminosilicate molecular sieves.

The use of certain novel non-zeolitic molecular sieves as "polymerization" catalysts to produce high boiling polymerization products is disclosed in copending: U.S. Ser. No. 400,438, filed July 26, 1982; U.S. Ser. No. 480,738, filed Mar. 31, 1983; U.S. Ser. No. 514,334, filed July 15, 1983; and U.S. Ser. No. 514,335, filed July 15, 1983. The interconversion of $C_2$, $C_3$ and $C_4$ olefins using certain non-zeolitic molecular sieves is not disclosed in the aforementioned applications. U.S. Pat. No. 4,310,440, discloses that aluminosphosphates ($AlPO_4$) may be employed as polymerization catalysts.

A process for the oligomerization olefins to hydrocarbon fuels is disclosed in U.S. Ser. No. 551,881 filed 11-15-83, commonly assigned. The instant invention is to be distinguished from the aforementioned oligomerization process by the selection of specific non-zeolitic molecular sieves for the instant olefin interconversion whereby less than 20 mole percent of the $C_2$ to $C_4$ olefins are converted to products containing greater than five carbons.

SUMMARY OF THE INVENTION

The instant process relates to the "interconversion" of ethylene, propylene and/or butenes using a non-zeolitic molecular sieves ("NZ-MS") as disclosed in U.S. Pat. No. 4,310,440 or a "NZ-MS" having a framework structure of $MO_2$, $AlO_2$ and $PO_2$ tetrahedra and having an empirical chemical composition on an anhydrous basis expressed by the formula:

$$mR: (M_xAl_yP_z)O_2$$

wherein "R" represents at least one organic templating agent present in the intracrystalline pore system; "m" represents the moles of "R" present per mole of $(M_xAl_yP_z)O_2$, "M" represents specific elements present other than aluminum and phosphorus in the form of a tetrahedral oxide, as hereinafter discussed, "x", "y" and "z" represent the mole fractions of "M", aluminum and phosphorus, respectively, present as tetrahedral oxides.

The non-zeolitic molecular sieves employed in the instant process are those disclosed in: U.S. Pat. No. 4,440,871, issued Apr. 3, 1984 (SAPOs wherein "M" is silicon); U.S. Ser. No. 480,738, filed Mar. 31, 1983 (TAPOs wherein "M" is titanium); U.S. Ser. No. 514,334, filed July 15, 1983 (MeAPOs wherein "Me" is at least one of magnesium, manganese, cobalt and zinc); and U.S. Pat. No. 4,310,440; U.S. Ser. No. 514,335, filed July 15, 1983 (FAPOs wherein "M" is iron). The aforementioned applications are incorporated herein by reference thereto. The acronyms "AlPO$_4$" "SAPO", "TAPO", "MeAPO" and "FAPO" and etc. are explained in the aforementioned applications and are briefly discussed hereinafter in the "DETAILED DESCRIPTION OF THE INVENTION."

The instant process comprises contacting an initial mixture containing at least one of ethylene, propylene and butenes with at least one of the aforementioned non-zeolitic molecular sieves at effective olefin interconversion conditions. The NZ-MSs employed in the instant process are further characterized by an adsorption for n-hexane of more than 2 percent by weight at a pressure of 400 torr and a temperature of 24.0° C. and by an adsorption for isobutane of less than 2 percent by weight at a pressure of 100 torr and a temperature of 24° C. The preferred molecular non-zeolitic sieves of this invention are characterized by specific x-ray powder diffraction data as set forth hereinafter.

DETAILED DESCRIPTION OF THE INVENTION

The instant process relates to the interconversion of at least one small olefin of the group consisting of ethylene, propylene, and butenes to one of the other olefins in the group. Accordingly, the invention relates to six olefin interconversions which may be carried out singularly or in combination, although in most instances more than one such interconversions will occur concurrently. The following conversions are those which define the term "olefin interconversion" as that term is employed herein:

(1) ethylene to propylene;
(2) ethylene to butenes;
(3) propylene to ethylene;
(4) propylene to butenes;
(5) butenes to ethylene; and
(6) butenes to propylene.

Further, the terms "small olefins" or "olefins" are employed herein to refer to ethylene, propylene, butenes, derivatives thereof and mixtures thereof. The term "butenes" is employed herein to refer to all butenes and butadienes. The derivatives of the "small olefins" may include functional groups which do not interfere with the interconversion to small olefins and derivatives thereof and may include substitution by functional groups such as halogen, cyanide, carboxylic acid, aldehyde and the like.

The process involves contacting such small olefins at effective olefin interconversion conditions with at least one "non-zeolite molecular sieve", ("NZ-MS"), as disclosed in U.S. Pat. No. 4,310,440 or a "NZ-MS" having a framework structure of $MO_2$, $AlO_2$ and $PO_2$ tetrahedra and having an empirical chemical composition on an anhydrous basis expressed by the formula:

MR: $(M_xAl_yP_z)O_2$ wherein "R" represents at least one organic templating agent present in the intracrystalline pore system; "m" represents the moles of "R" present per mole of $(M_xAl_yP_z)O_2$, "M" represents silicon, iron, titanium or at least one of magnesium, manganese, cobalt and zinc, such being present in the form of a tetrahedral oxide; and "x", "y" and "z" represent the mole fractions of "m", aluminum and phosphorus, respectively, present as tetrahedral oxides.

The term "non-zeolitic molecular sieve" or the abbreviation "NZ-MS" is employed herein to denominate the molecular sieve compositions described in U.S. Pat. No. 4,440,871, copending U.S. Ser. Nos. 480,738, 514,334 and 514,335, and in U.S. Pat. No. 4,310,440 as hereinbefore mentioned and incorporated by reference thereto. These non-zeolitic molecular sieves are employed herein to provide the instant interconversion of ethylene propylene and butenes.

The NZ-MS employed in the instant process are further characterized by an adsorption for n-hexane of more than 2 percent by weight at a pressure of 400 torr and a temperature of 24.0° C. and by an adsorption for isobutane of less than 2 percent by weight at a pressure 100 torr and a temperature of 24° C. The preferred non-zeolitic molecular sieves for use in the instant process are characterized by x-ray diffraction patterns as set forth in Table A, Table B or Table C or Table D, or Table E or Table F:

TABLE A

| 2θ | d(A) | Relative Intensity |
|---|---|---|
| 7.70–7.75 | 11.5–11.4 | vs |
| 13.4 | 6.61 | s–vs |
| 15.5–15.55 | 5.72–5.70 | s |
| 19.65–19.7 | 4.52–4.51 | w–s |
| 20.5–20.6 | 4.33–4.31 | vs |
| 31.8–32.00 | 2.812–2.797 | w–s |

TABLE B

| 2θ | d(A) | Relative Intensity |
|---|---|---|
| 9.60–9.65 | 9.21–9.16 | vs |
| 15.5–15.55 | 5.72–5.70 | m |
| 16.9–17.1 | 5.25–5.19 | m |
| 20.15–20.25 | 4.41–4.39 | m |
| 20.95–21.05 | 4.24–4.22 | m |
| 31.8–32.5 | 2.814–2.755 | m |

TABLE C

| 2θ | d(A) | Relative Intensity |
|---|---|---|
| 9.4–9.65 | 9.41–9.17 | s–vs |
| 15.9–16.2 | 5.57–5.47 | vw–m |
| 17.85–18.4 | 4.97–4.82 | w–s |
| 20.3–20.9 | 4.37–4.25 | m–vs |

TABLE C-continued

| 2θ | d(A) | Relative Intensity |
|---|---|---|
| 24.95–25.4 | 3.57–3.51 | vw–s |
| 30.3–30.8 | 2.95–2.90 | w–s |

TABLE D

| 2θ | d(A) | Relative Intensity |
|---|---|---|
| 10.8–11.1 | 8.19–7.97 | m |
| 17.2–17.4 | 5.16–5.10 | s–vs |
| 21.0–21.25 | 4.23–4.18 | m–s |
| 21.8–22.0 | 4.08–4.04 | vs |
| 31.8–32.2 | 2.814–2.788 | m |

TABLE E

| 2θ | d(A) | Relative Intensity |
|---|---|---|
| 9.4–9.55 | 9.41–9.26 | vs |
| 13.0–13.1 | 6.81–6.76 | w–m |
| 16.0–16.2 | 5.54–5.47 | w–m |
| 20.6–20.85 | 4.31–4.26 | s–vs |
| 24.3–24.4 | 3.66–3.65 | w–vs |
| 30.7–30.95 | 2.912–2.889 | w–s |

TABLE F

| 2θ | d(A) | Relative Intensity |
|---|---|---|
| 9.4 | 9.41 | vs |
| 15.9–16.0 | 5.57–5.54 | w–m |
| 20.5–20.6 | 4.33–4.31 | s |
| 24.5–24.7 | 3.63–3.60 | w |
| 25.8–25.9 | 3.45–3.44 | w |
| 30.4–30.5 | 2.940–2.931 | w |

The class members of the molecular sieves set forth in the above identified copending applications are referred to therein by a series of abbreviations. These abbreviations include: $AlPO_4$, SAPO, FeAPO, CoAPO, MAPO, MnAPO, TAPO, and ZAPO where each acronym is as defined in the above referenced applications. The members of each class, e.g., the members of the SAPO class, MAPO class or ZAPO class, are characterized by referring to class members as a "-n" member, e.g., as SAPO-5, MnAPO-11, ZAPO-34 and etc., wherein the "n" designation is a number specific to a given class member as its preparation is reported in the aforementioned copending applications. For the sake of convenient reference the aforementioned non-zeolitic molecular sieves, i.e. those disclosed in the above copending patent applications, will be generally referred to herein as the "NZ-MS" molecular seives. Individual members of the class of "NZ-MSs" will be referred to by the nomenclature assigned to that class member as such is denominated in a particular referenced application.

The effective olefin interconversion conditions employed in the instant process, such as temperature, pressure, space velocity and molar ratio of any co-fed diluent to the small olefin, will have an affect on the process. In general the process is carried out at effective interconversion conditions such that interconversion of said starting olefin occurs and such that less than 20 mole percent, preferably less than 10 mole percent, of the starting small olefin(s) is converted to products having a carbon number greater than five (5).

The instant small olefin interconversion process may be carried out in either the liquid-phase or the vapor-phase by contacting the NZ-MS and the small olefin(s) in a reaction zone, such as, for example, a fixed bed of catalyst, under effective olefin interconversion conditions. The process may be conducted in either batch or fluid bed operation with attendant benefits of either operation readily obtainable.

The effective olefin interconversion conditions employed in carrying out the instant process include an effective temperature(s), pressure(s), weight hourly space velocity, contact time(s) and, if employed, an effective amount of diluent. The process is generally carried out at an effective temperature between about 150° C. and about 600° C., preferably between about 200° C. and about 550° C., and at effective pressures ranging between about 0.1 atmosphere (14.7 psia) up to about 100 atmospheres or higher, although subatmospheric pressures may be employed. The pressure is preferably between about 1 and about 50 atmospheres. The weight hourly space velocity (WHSV) of the olefins is generally maintained at between about 0.01 $hr^{-1}$ and about 100 $hr^{-1}$ and is preferably between about 0.1 $hr^{-1}$ and about 40 $hr^{-1}$.

The instant olefin interconversion process may employ an effective amount of diluent in the process, including, but not limited to: $C_1$-$C_4$ paraffins; methane; ethane; propane; isobutane and n-butane; inert gases, such as nitrogen, carbon dioxide; water (and/or steam); and hydrogen.

The effective amount of diluent which may be employed in the instant process is not narrowly critical, although specific effective amounts of some diluents may exist, e.g., water. The amount of diluent may vary within the range of from 0 to about 99 weight percent, more preferably between about 1 and about 95 weight percent, based on the total weight of small olefin(s) and diluent. The amount of diluent is more preferably within the range between about 10 and about 70 weight percent. The NZ-MS catalysts, as above defined for use herein, may be particularly benefited by co-fed water which may aid in resisting coking and aging of the NZ-MS containing catalyst.

It has been found that the NZ-MS class of non-zeolitic molecular sieves can be employed in the present process to provide for the selective interconversion of small olefins selected from the group consisting of ethylene, propylene, butenes and mixtures thereof to one of the other olefins of the aforementioned group. The products of the present process contain primarily small olefins and generally contain less than 20 percent by weight of products containing five carbons or greater.

The NZ-MS catalysts employed in the instant invention may have a certain proportion of the original cations associated therewith replaced by a wide variety of other cations according to techniques well known in the art. Typical replacing cations include hydrogen, ammonium and alkali and alkaline earth metal cations, including mixtures of the same.

Typical ion exchange techniques involve contacting the particular non-zeolitic molecular sieve (NZ-MS) with a salt of the desired replacing cation or cations. Although a wide variety of soluble salts can be employed, particular preference is given to chlorides, nitrates and sulfates owing to their solubility in water since water is the preferred solvent for such ion exchange techniques. Representative ion exchange techniques are disclosed in a wide variety of patents including U.S. Pat. No. 3,140,249; 3,140,251; and 3,140,253. Following contact with the ion exchange solution of the desired replacing cation, the NZ-MS may be washed with water and dried.

One embodiment of this invention resides in the use of a porous matrix with the NZ-MS catalysts previously described. The NZ-MS can be combined, dispersed or otherwise intimately admixed with a porous matrix in such proportions that the resulting product contains from 1% to 95% by weight, and preferably from 20% to 80% by weight, of the NZ-MS in the final catalyst composite. The catalysts may be formed by standard catalyst forming techniques including spray-drying, pelleting, extrusion and other suitable conventional means.

The term "porous matrix" includes active or inactive inorganic compositions with which the NZ-MS can be combined, dispersed or otherwise intimately admixed. It is to be understood that the porosity of the compositions employed as a matrix can either be inherent in the particular material or it can be introduced by mechanical or chemical means. Representative matrices which can be employed include metals and alloys thereof, sintered metals and sintered glass, asbestos, silicon carbide aggregates, pumice, firebrick, diatomaceous earths, aluminosilicates and inorganic oxides. Inorganic compositions especially those of a siliceous nature are preferred. Of these matrices, inorganic oxides such as clay, chemically treated clay, silica, silica-aluminum, etc., are particularly preferred because of their superior porosity, attrition resistance and stability.

The inorganic oxide may also consist of raw clay or a clay mineral which has been treated with an acid medium to render it active. The NZ-MS may be incorporated with the clay simply by blending the two and fashioning the mixture into desired shapes. Suitable clays include attapulgite, kaoline, sepiolite, poly-garskite, kaolinte, halloysite, plastic ball clays, bentonite, montmorillonite, illite, chlorite, etc. Other useful matrices include powders of refractory oxides, such as alumina, alpha alumina, etc., having very low internal pore volume. Preferably, these materials are inert with respect to the instant reactions, having substantially no inherent catalytic activity of their own.

Final catalysts comprising at least one NZ-MS may be heated in steam or in other atmospheres, e.g., air, at the temperature contemplated for conversion or may be heated to operating temperatures initially during use in the process or may be calcined in air, steam, nitrogen, helium flue gas, or other gases not harmful to the catalyst product, at temperatures ranging from about 500° F. to 1600° F. and for periods of time ranging from 1 to 48 hours or more. It is to be understood that the NZ-MS may also be calcined prior to incorporation with a matrix. It is to be further understood that the NZ-MS need not be ion exchanged prior to incorporation into a matrix but can be so treated during or after such incorporation.

EXPERIMENTAL PROCEDURE

The olefin interconversion set forth in the examples were carried out by mixing about 0.4 to 0.5 grams of a selected NZ-MS with about 0.75 to 2.5 grams of quartz chips (20-30 U.S. Standard mesh). The resulting mixture was then placed in a ¼ inch (outside diameter) No. 304 stainless steel tubular reactor having a wall thickness of 0.035 inch. The tubular reactor was immersed in a fluidized heated sand bath having electrical resistance heaters provided for maintaining the sand bath and the tubular reactor at the desired temperature. Thermocouples were provided for measurement of the reactor temperature.

A selected small olefin was introduced to the tubular reactor either alone or concurrently with a stream of a diluent. The pressure employed in the examples was the autogenous pressure (about one (1) to about three (3) atmospheres unless otherwise noted. The flow rates of the small olefin(s) and diluent are set forth in each example in cubic centimeters per minute ($cm^3$/min). The effluent from the tubular reactor (the reaction products) was analyzed.

The conversion to products is based on the small olefin(s) present in the final reaction mixture with the yield to a particular small olefin being given as the mole percentage of that small olefin in the final reaction mixture. When a product was not detected or if the amount was not capable of being quantitatively detected such is reported as zero.

The following examples are provided to exemplify the invention and are not meant to be limiting in any way.

EXAMPLES 1 TO 9

SAPO-34 was evaluated according to the EXPERIMENTAL PROCEDURE for the interconversion of ethylene, propylene and butenes. The SAPO-34 was prepared according to the disclosure of U.S. Pat. No. 4,440,871, had an adsorption of n-hexane of greater than 2 percent by weight at a pressure of 400 torr and a temperature of 24° C. and an adsorption of isobutane of less than 2 percent by weight at a pressure of 100 torr and a temperature of 24° C. and was characterized by the x-ray diffraction pattern of Table C. The feed for each interconversion and the process conditions are identified in Tables I to IX. The percent of each component in the feed is based on a volume percent and the product analysis is based on a mole percent.

The results in Tables I to IX demonstrate that SAPO-34 provides for the interconversion of ethylene to propylene and butenes with less than 20 mole percent products containing greater than five carbons.

TABLE I (Example 1)[1]

| | | | |
|---|---|---|---|
| Methane | 0.00 | 0.00 | 0.00 |
| Carbon Dioxide | 0.44 | 0.15 | 0.05 |
| Ethylene | 22.93 | 10.18 | 15.60 |
| Ethane | 1.78 | 2.52 | 4.01 |
| Propylene | 18.56 | 20.60 | 37.85 |
| Propane | 35.68 | 42.90 | 16.92 |
| Butenes | 16.92 | 18.11 | 19.83 |
| $C_5$ | 2.98 | 4.70 | 4.90 |
| $C_6$ | 0.73 | 0.83 | 0.80 |
| Run Times, Hrs. | 0.5 | 1.25 | 2.08 |

[1]The feed was a mixture of 85 volume percent nitrogen and 15 volume percent ethylene. The total flow rate was 5 $cm^3$/min, the temperature was 375° C. and the pressure was the autogenous pressure.

TABLE II (Example 2)[1]

| | Run a | | | | Run b | |
|---|---|---|---|---|---|---|
| Methane | 0.50 | 0.17 | 0.19 | 0.00 | 0.06 | 0.00 |
| Carbon Dioxide | 0.62 | 0.26 | 0.22 | 0.07 | 0.03 | 0.02 |
| Ethylene | 13.49 | 44.00 | 51.65 | 69.06 | 78.17 | 82.92 |
| Ethane | 4.44 | 2.79 | 2.49 | 1.30 | 1.22 | 1.00 |
| Propylene | 37.44 | 43.81 | 38.99 | 27.26 | 18.82 | 15.05 |
| Propane | 12.79 | 0.00 | 0.00 | 0.00 | 0.00 | 0.00 |
| Butenes | 23.19 | 8.43 | 5.76 | 2.00 | 1.63 | 0.94 |
| $C_5$ | 5.41 | 0.85 | 0.61 | 0.30 | 0.06 | 0.08 |
| $C_6$ | 0.83 | 0.12 | 0.09 | 0.00 | 0.00 | 0.00 |

TABLE II-continued (Example 2)[1]

| | Run a | | | Run b | | |
|---|---|---|---|---|---|---|
| Run Times, Hrs. | 0.75 | 1.42 | 2.0 | 0.5 | 1.25 | 2.0 |

[1]The feed was a mixture of 50 percent ethylene and 50 percent nitrogen; the total flow rate was 5 $cm^3$/min in "Run a" and 10 $cm^3$/min in "Run b"; the temperature in "Run a" and "Run b" was 375° C.; and the same catalyst charge was employed in "Run a" and "Run b". This catalyst was treated at 500° C. in air for 3 hours prior to "Run a".

TABLE III (Example 3)[1]

| | | | |
|---|---|---|---|
| Methane | 0.00 | 0.00 | 0.00 |
| Carbon Dioxide | 0.00 | 0.00 | 0.00 |
| Ethylene | 1.78 | 1.07 | 0.85 |
| Ethane | 0.03 | 0.02 | 0.01 |
| Propylene | 11.77 | 6.20 | 4.33 |
| Propane | 0.75 | 0.16 | 0.05 |
| Butenes | 83.87 | 91.50 | 94.22 |
| $C_5$ | 1.66 | 0.71 | 0.48 |
| $C_6$ | 0.11 | 0.32 | 0.04 |
| Run Times, Hrs. | 0.5 | 1.41 | 2.25 |

[1]The feed was mixture of 1-butene and nitrogen each provided at a flow rate of 5 $cm^3$/min for a total flow rate of 10 $cm^3$/min. and the temperature was 375° C. This catalyst was treated at 500° C. in air for 2 hours prior to use.

TABLE IV (Example 4)[1]

| | | | |
|---|---|---|---|
| Methane | 0.13 | 0.00 | 0.00 |
| Carbon Dioxide | 0.04 | 0.00 | 0.03 |
| Ethylene | 6.36 | 3.63 | 2.92 |
| Ethane | 0.08 | 0.02 | 0.00 |
| Propylene | 62.90 | 88.60 | 93.14 |
| Propane | 5.61 | 0.00 | 0.00 |
| Butenes | 25.71 | 6.69 | 3.48 |
| $C_5$ | 4.99 | 0.63 | 0.20 |
| $C_6$ | 0.79 | 0.43 | 0.23 |
| Run Times, Hrs. | 0.5 | 1.25 | 2.0 |

[1]The feed was a mixture of: (a) 50/50 percent mixture of propylene and nitrogen and (b) water; where the flow rate of propylene/nitrogen was 10 $cm^3$/min. and of water was 1.6 $cm^3$/hr.; and the temperature was 375° C. This catalyst was treated at 500° C. in air for 2 hours prior to use.

TABLE V (Example 5)[1]

| | | | |
|---|---|---|---|
| Methane | 0.14 | 0.00 | 0.00 |
| Carbon Dioxide | 0.02 | 0.00 | 0.00 |
| Ethylene | 7.49 | 6.62 | 4.31 |
| Ethane | 0.31 | 0.10 | 0.02 |
| Propylene | 64.42 | 85.92 | 92.28 |
| Propane | 0.00 | 0.00 | 0.00 |
| Butenes | 17.20 | 6.44 | 2.91 |
| $C_5$ | 2.33 | 0.48 | 0.20 |
| $C_6$ | 0.76 | 0.42 | 0.25 |
| Run Times, Hrs. | 0.5 | 1.33 | 2.5 |

[1]The feed was a mixture of 50 percent propylene and 50 percent nitrogen; the temperature was 375° C.; and the flow rate was 10 $cm^3$/min. This catalyst was treated at 500° C. in air for 2 hours prior to use.

TABLE VI (Example 6)[1]

| | Run a | | | Run b | | |
|---|---|---|---|---|---|---|
| Methane | 0.82 | 0.49 | 0.37 | 0.76 | 0.34 | 0.24 |
| Carbon Dioxide | 0.08 | 0.04 | 0.03 | 0.05 | 0.05 | 0.04 |
| Ethylene | 36.03 | 59.53 | 71.39 | 11.02 | 8.35 | 6.25 |
| Ethane | 3.80 | 2.66 | 2.08 | 0.67 | 0.23 | 0.13 |
| Propylene | 50.54 | 33.80 | 23.88 | 77.08 | 86.94 | 90.75 |
| Propane | 0.00 | 0.00 | 0.00 | 0.00 | 0.00 | 0.00 |
| Butenes | 7.43 | 3.10 | 1.97 | 8.25 | 3.01 | 1.72 |
| $C_5$ | 0.90 | 0.29 | 0.21 | 0.98 | 0.30 | 0.23 |
| $C_6$ | 0.39 | 0.10 | 0.08 | 1.19 | 0.78 | 0.64 |

TABLE VI-continued

| (Example 6)[1] | | | | | | |
|---|---|---|---|---|---|---|
| | Run a | | | Run b | | |
| Run Times, Hrs. | 1.00 | 1.75 | 2.5 | 1.00 | 1.8 | 2.5 |

[1]The feed was ethylene in "Run a" and propylene in "Run b"; the flow rate was 5 cm³/min in "Run a" and 4.4 cm³/min in "Run b"; the temperature was 375° C. in each run; and the same catalyst charge was employed in each run. The catalyst was treated at 500° C. in air for 3.5 hours prior to use in each run.

TABLE VII

| (Example 7)[1] | | |
|---|---|---|
| Methane | 0.00 | 0.00 |
| Carbon Dioxide | 0.03 | 0.02 |
| Ethylene | 1.20 | 0.68 |
| Ethane | 0.02 | 0.01 |
| Propylene | 0.76 | 0.36 |
| Propane | 0.55 | 0.18 |
| Butenes | 97.41 | 98.41 |
| $C_5$ | 0.00 | 0.00 |
| $C_6$ | 0.00 | 0.00 |
| Run Time, Hrs. | 0.5 | 1.33 |

[1]The feed was a mixture of 1,3 butadiene and nitrogen formed by mixing each at a flow rate of 5 cm³/min. for a total flow rate of 10 cm³/min.; and the temperature was 375° C.

TABLE VIII

| (Example 8)[1] | | | |
|---|---|---|---|
| Methane | 0.12 | 0.01 | 0.00 |
| Carbon Dioxide | 0.00 | 0.00 | 0.00 |
| Ethylene | 2.18 | 0.56 | 0.31 |
| Ethane | 0.51 | 0.00 | 0.00 |
| Propylene | 6.47 | 1.11 | 0.80 |
| Propane | 0.20 | 0.04 | 0.00 |
| Butenes | 89.29 | 97.90 | 98.29 |
| $C_5$ | 0.75 | 0.10 | 0.05 |
| $C_6$ | 0.10 | 0.14 | 0.00 |
| Run Times, Hrs. | 0.5 | 1.75 | 2.75 |

[1]The feed was a mixture of 1-butene and nitrogen formed by mixing each at a flow rate of 5 cm³/min. for a total flow rate of 10 cm³/min.; and the temperature was 425° C. The catalyst was treated at 500° C. in air for 6 hours prior to use.

TABLE IX

| (Example 9)[1] | | | |
|---|---|---|---|
| Methane | 1.22 | 0.11 | 0.00 |
| Carbon Dioxide | 0.02 | 0.00 | 0.00 |
| Ethylene | 12.57 | 9.46 | 5.38 |
| Ethane | 1.08 | 0.17 | 0.03 |
| Propylene | 57.98 | 83.42 | 90.76 |
| Propane | 3.58 | 0.00 | 0.00 |
| Butenes | 19.33 | 5.87 | 3.15 |
| $C_5$ | 3.08 | 0.32 | 0.11 |
| $C_6$ | 1.15 | 0.65 | 0.56 |
| Run Times, Hrs. | 0.5 | 1.33 | 2.5 |

[1]The feed was a mixture of 50 volume percent propylene and 50 volume percent nitrogen; the flow rate was 10 cm³/min.; and the temperature was 425° C. The catalyst was treated at 500° C. in air for 4 hours prior to use.

EXAMPLES 10 AND 11

MAPO-34 (where "M" is Mg) was employed for the interconversion of propylene to ethylene and butylene (Example 10) and of ethylene to propylene and butenes (Example 11). MAPO-34 was prepared in accordance with the disclosure of copending U.S. Ser. No. 514,334, filed July 15, 1983, was characterized by the same n-hexane and isobutane adsorption observed for the SAPO-34 of examples 1 to 9 and was characterized by the x-ray diffraction pattern of Table C.

MAPO-34 formed no $C_5$ or $C_6$ products but did form mixtures of small olefins from the starting small olefin.

TABLE X

| (Example 10)[1] | | | |
|---|---|---|---|
| Methane | 0.04 | 0.00 | 0.00 |
| Carbon Dioxide | 0.00 | 0.00 | 0.00 |
| Ethylene | 2.24 | 1.16 | 0.79 |
| Ethane | 0.45 | 0.21 | 0.13 |
| Propylene | 96.30 | 98.38 | 98.94 |
| Propane | 0.00 | 0.00 | 0.00 |
| Butenes | 1.00 | 0.20 | 0.14 |
| $C_5$ | 0.00 | 0.00 | 0.00 |
| $C_6$ | 0.00 | 0.00 | 0.00 |
| Run Times, Hrs. | 0.5 | 1.3 | 2.0 |

[1]The feed was a mixture of 50 percent propylene and 50 percent nitrogen; the flow rate was 10 cm³/min.; and the temperature was 375° C.

TABLE XI

| (Example 11)[1] | | | |
|---|---|---|---|
| Methane | 0.00 | 0.00 | 0.00 |
| Carbon Dioxide | 0.00 | 0.03 | 0.03 |
| Ethylene | 93.57 | 97.53 | 97.67 |
| Ethane | 0.48 | 0.18 | 0.14 |
| Propylene | 4.68 | 1.65 | 1.68 |
| Propane | 0.92 | 0.48 | 0.40 |
| Butenes | 0.28 | 0.79 | 0.05 |
| $C_5$ | 0.00 | 0.00 | 0.00 |
| $C_6$ | 0.00 | 0.00 | 0.00 |
| Run Times, Hrs. | 0.5 | 1.25 | 2.0 |

[1]The feed mixture was a mixture of 50 percent ethylene and 50 percent nitrogen; the flow rate was 10 cm³/min.; and the temperature was 375° C. The catalyst was treated at 500° C. in air for 2 hours prior to use.

EXAMPLES 12 TO 14

AlPO$_4$-17, as disclosed in U.S. Pat. No. 4,310,440, was evaluated for: the interconversion of propylene to ethylene and butenes (Example 12); the interconversion of ethylene to propylene and butenes (Example 13); and the interconversion of 1-butene to ethylene and propylene (Example 14).

TABLE XII

| (Example 12)[1] | | | |
|---|---|---|---|
| Methane | 0.35 | 0.55 | 0.26 |
| Carbon Dioxide | 1.77 | 1.78 | 1.14 |
| Ethylene | 0.03 | 0.04 | 0.02 |
| Ethane | 0.00 | 0.00 | 0.00 |
| Propylene | 96.98 | 96.81 | 98.00 |
| Propane | 0.00 | 0.00 | 0.00 |
| Butenes | 0.31 | 0.19 | 0.10 |
| $C_5$ | 0.03 | 0.10 | 0.07 |
| $C_6$ | 0.50 | 0.49 | 0.38 |
| Run Times, Hrs. | 0.5 | 1.16 | 2.0 |

[1]The feed was a mixture of 50 percent propylene and 50 percent nitrogen; the flow rate was 10 cm³/min.; and the temperature was 425° C. The catalyst was treated at 500° C. in air for one hour prior to use.

TABLE XIII

| (Example 13)[1] | | | |
|---|---|---|---|
| Methane | 0.40 | 0.00 | 0.00 |
| Carbon Dioxide | 1.93 | 0.25 | 0.11 |
| Ethylene | 94.42 | 98.35 | 95.06 |
| Ethane | 0.09 | 0.00 | 0.00 |
| Propylene | 2.15 | 1.40 | 1.33 |
| Propane | 0.00 | 0.00 | 0.00 |
| Butenes | 1.00 | 0.00 | 0.00 |
| $C_5$ | 0.00 | 0.00 | 0.00 |
| $C_6$ | 0.00 | 0.00 | 0.00 |
| Run Times, Hrs. | 0.5 | 1.5 | 2.16 |

[1]The feed was a mixture of 50 percent ethylene and 50 percent nitrogen; the flow rate was 10 cm³/min.; and the temperature was 425° C. The catalyst was treated at 500° C. in air for one hour prior to use.

TABLE XIV (Example 14)[1]

| | | |
|---|---|---|
| Methane | 0.03 | 0.00 |
| Carbon Dioxide | 0.13 | 0.08 |
| Ethylene | 0.16 | 0.13 |
| Ethane | 0.00 | 0.00 |
| Propylene | 0.26 | 0.32 |
| Propane | 0.00 | 0.00 |
| Butenes | 99.42 | 99.47 |
| $C_5$ | 0.00 | 0.02 |
| $C_6$ | 0.00 | 0.00 |
| Run Time, Hrs. | 0.5 | 1.41 |

[1]The feed was a mixture of 50 percent 1-butene and 50 percent nitrogen; the flow rate was 5 cm$^3$/min.; and the temperature was 375° C. The catalyst was treated at 500° C. in air for two hours prior to use.

I claim:

1. Process for the interconversion of ethylene, propylene and butenes comprising contacting an olefin feed containing at least one of ethylene, propylene and butenes with at least one molecular sieve selected from the group consisting of the SAPOs of U.S. Pat. No. 4,440,871 and the AlPO$_4$s of U.S. Pat. No. 4,310,440 characterized by an adsorption for n-hexane of more than 2 percent by weight at 400 torr and at 24.0° C. and by an adsorption for isobutane of less than 2 percent by weight at a pressure of 100 torr and a temperature of 24° C., at effective olefin interconversion conditions for forming small olefin products.

2. The process of claim 1 wherein said molecular sieve is SAPO.

3. The process of claims 1 or 2 wherein said molecular sieve has an x-ray diffraction pattern characterized by Table A.

4. The process of claims 1 or 2 wherein said molecular sieve has an x-ray diffraction pattern characterized by Table B.

5. The process of claims 1 or 2 wherein said molecular sieve has the x-ray diffraction pattern characterized by Table C.

6. The process of claims 1 or 2 wherein said molecular sieve has the x-ray diffraction pattern characterized by Table D.

7. The process of claims 1 or 2 wherein said molecular sieve has the x-ray diffraction pattern characterized by Table E.

8. The process of claims 1 or 2 wherein said molecular sieve has the x-ray diffraction characterized by Table F.

9. The process of claim 1 wherein less than 20 percent of weight of the small olefins is converted to products having a carbon number greater than five.

10. The process of claims 1 or 2 wherein said olefin feed consists essentially of at least one of ethylene, propylene and butenes.

11. The process of claim 1 wherein the process is carried out in the vapor phase.

12. The process of claim 1 wherein the process is carried out in the liquid phase.

13. The process of claim 1 wherein said process is carried out in the presence of a diluent.

14. The process of claim 13 wherein the diluent is selected from the class consisting of $C_1$ to $C_4$ paraffins, nitrogen, carbon dioxide, water and mixtures thereof.

15. The process of claim 14 wherein the diluent is water.

16. The process of claim 15 wherein the diluent is nitrogen.

17. The process of claim 1 wherein said molecular seive is an AlPO$_4$.

* * * * *